United States Patent
Chen

(10) Patent No.: US 9,427,409 B2
(45) Date of Patent: Aug. 30, 2016

(54) COMPOSITION AND METHOD FOR AIDING SLEEP

(71) Applicant: Sequential Medicine Limited, Grand Cayman (KY)

(72) Inventor: Lan Bo Chen, Lexington, MA (US)

(73) Assignee: Sequential Medicine Limited, Grand Cayman (KY)

( * ) Notice: Subject to any disclaimer, the term of this patent is extended or adjusted under 35 U.S.C. 154(b) by 0 days.

(21) Appl. No.: 14/614,916

(22) Filed: Feb. 5, 2015

(65) Prior Publication Data

US 2015/0216811 A1 Aug. 6, 2015

Related U.S. Application Data

(60) Provisional application No. 61/936,566, filed on Feb. 6, 2014.

(51) Int. Cl.

| | |
|---|---|
| *A61K 31/135* | (2006.01) |
| *A61K 31/5513* | (2006.01) |
| *A61K 31/437* | (2006.01) |
| *A61K 9/00* | (2006.01) |
| *A61K 9/22* | (2006.01) |
| *A61P 25/20* | (2006.01) |
| *A61K 9/50* | (2006.01) |
| *A61K 31/5517* | (2006.01) |
| *A61K 9/20* | (2006.01) |

(52) U.S. Cl.
CPC ........... *A61K 9/5026* (2013.01); *A61K 31/135* (2013.01); *A61K 31/437* (2013.01); *A61K 31/5513* (2013.01); *A61K 31/5517* (2013.01); *A61K 9/2086* (2013.01)

(58) Field of Classification Search
CPC ........... A61K 2300/00; A61K 31/135; A61K 31/437; A61K 31/5513; A61K 9/2086; A61K 9/5026; A61K 31/5517; A61K 9/0053
See application file for complete search history.

(56) References Cited

U.S. PATENT DOCUMENTS

| | | | | |
|---|---|---|---|---|
| 6,340,476 | B1 * | 1/2002 | Midha | A61K 45/06 424/451 |
| 6,485,746 | B1 * | 11/2002 | Campbell | A61K 9/209 424/468 |
| 2005/0031688 | A1 | 2/2005 | Ayala | |
| 2006/0084659 | A1 * | 4/2006 | Davis | A61K 31/195 514/252.16 |
| 2007/0082048 | A1 * | 4/2007 | Warner | A61K 9/0007 424/464 |
| 2008/0248103 | A1 | 10/2008 | Heuer et al. | |
| 2008/0254121 | A1 | 10/2008 | Clement et al. | |
| 2009/0297601 | A1 * | 12/2009 | Vergnault | A61K 9/2813 424/474 |
| 2010/0055181 | A1 * | 3/2010 | Bhandari | A61K 9/2054 424/482 |
| 2011/0262539 | A1 * | 10/2011 | Bosse | A61K 9/2054 424/472 |
| 2013/0078304 | A1 | 3/2013 | Hsieh et al. | |
| 2013/0122092 | A1 | 5/2013 | Stankov | |

FOREIGN PATENT DOCUMENTS

CH        WO 9816231 A1 *   4/1998   ............ A61K 31/55

OTHER PUBLICATIONS

Kudo et al., J. Clin. Pharmacol, 1990, 30, 1041-1048.*
Holm et al. "Zolpidem: An Update of its Pharmacology, Therapeutic Efficacy and Tolerability in the Treatment of Insomnia" Drugs vol. 59, pp. 865-889. 2000.
Lee. "Overview of the Therapeutic Management of Insomnia with Zolpidem" CNS Drugs vol. 18, pp. 17-23. 2004.
Cluydts. "Zolpidem 'As Needed': Methodological Issues and Clinical Findings" CNS Drugs vol. 18, pp. 25-33. 2004.
Hajak et al. "Experience with Zolpidem 'As Needed' in Primary Care Settings" CNS Drugs vol. 18, pp. 35-40. 2004.
Cluydts. "Zolpidem 'As Needed': A New Treatment Paradigm" CNS Drugs vol. 18, p. 41. 2004.
"Questions and Answers" CNS Drugs vol. 18, pp. 43-53. 2004.
Allaert et al. "Sociodemographic Profile of Insomniac Patients Across National Surveys" CNS Drugs vol. 18, pp. 3-7. 2004,.
Sanger. "The Pharmacology and Mechanisms of Action of New Generation, Non-Benzodiazepirie Hypnotic Agents" CNS Drugs vol. 18, pp. 9-15. 2004.
Roehrs et al. "Insomnia Pharmacotherapy" Neurotherapeutics vol. 9, pp. 728-238. 2012.
Lui et al. "Comparison of Gastrointestinal pH in Dogs and Humans: Implications on the Use of the Beagle Dog as a Model for Oral Absorption in Humans" Journal of Pharmaceutical Sciences vol. 75, pp. 271-274. 1986.

* cited by examiner

*Primary Examiner* — Abigail Fisher
(74) *Attorney, Agent, or Firm* — Cesari and McKenna, LLP

(57) ABSTRACT

Described is a controlled-release formulation for treating disturbed sleep or insomnia in a subject. The formulation is formulated to release a compound or combination of compounds in sequence at multiple stages.

7 Claims, No Drawings

COMPOSITION AND METHOD FOR AIDING SLEEP

CROSS REFERENCE TO RELATED APPLICATION

This application claims priority to U.S. Provisional Patent Application No. 61/936,566, filed on Feb. 6, 2014, the entire content of which is hereby incorporated by reference herein.

BACKGROUND

In patients suffering sleep disruptions, one can observe a clear distinction between the ability to fall asleep and the ability to remain asleep long enough to feel rested. Pharmacological therapeutics for insomnia typically focus on enabling a patient to fall asleep. Most patients taking sleeping pills wake up in the middle of night without completing the 8-hour sleep cycle. There is a need for drugs that allow a patient to fall asleep and stay asleep for a sufficient period of time.

SUMMARY

Described below is a controlled-release formulation. The formulation includes one or more compounds for aiding sleep, wherein the formulation is formulated for releasing each compound at a specific time and a specific dose in a subject after the formulation is administered to the subject.

In one embodiment, the formulation is formulated for two to twelve stages of release, wherein each stage initiates release of a compound or a combination of compounds in a subject at a specific time point after administration of the formulation to the subject. For example, the time interval between the initiation of each stage of release can be 0.5 to 23 hours. The first stage can be for immediate release of a compound or combination of compounds.

The compound or compounds can be selected from the group consisting of barbiturates (e.g., amobarbital (Amytal), pentobarbital (Nembutal), secobarbital (Seconal), and phenobarbital (Luminal); benzodiazepines (e.g., clonazepam (Klonopin N. America; Rivotril Europe, Asia), diazepam (Valium), estazolam (Prosom), flunitrazepam (Rohypnol), lorazepam (Ativan), midazolam (Versed), nitrazepam (Mogadon), oxazepam (Serax), triazolam (Halcion), temazepam (Restoril, Normison, Planum, Tenox, and Temaze), chlordiazepoxide (Librium), and alprazolam (Xanax)); non-benzodiazepine "Z-drugs" sedatives (e.g., eszopiclone (Lunesta), zaleplon (Sonata), zolpidem (Ambien), and zopiclone (Imovane, Zimovane)); antihistamines (e.g., diphenhydramine, dimenhydrinate, doxylamine, mirtazapine, and promethazine); plant components or extracts (from, e.g., *Duboisia hopwoodii*, chamomile, *Prostanthera striatiflora*, catnip, kava (*Piper methysticum*), valerian, *cannabis*, and *passiflora* (e.g., *Passiflora incarnata*)); Validol; chloral hydrate; trazodone; opiates and opioids; Suvorexant (MK-4305, Merck & Co.); glutethimide; and γ-hydroxybutyric acid.

In one embodiment, the formulation is a tablet or capsule for oral administration. The tablet or capsule can contain a plurality of particles, each particle including a drug core and a polymeric composition encapsulating the core, wherein the drug core contains the one or more compounds for aiding sleep.

Also described is a method of treating disturbed sleep or insomnia in a subject. The method includes administering the above-described formulation to a subject in need thereof.

The details of one or more embodiments are set forth in the description below. Other features, objects, and advantages of the embodiments will be apparent from the description and from the claims.

DETAILED DESCRIPTION

It was unexpectedly discovered that administering certain drugs or combinations of drugs sequentially can both induce and maintain sleep in patients having disturbed sleep or insomnia. This approach extends sleep time while utilizing lower than recommended doses of the drugs, which reduces the risk of addiction and other side effects (e.g., next-morning impairment).

Disturbed Sleep

As used herein, the term "disturbed sleep", "sleep disturbances," or "sleep disruption" refers to a condition characterized by waking up feeling unrestored, waking up in the middle of the night, difficulty returning to sleep after waking, difficulty falling asleep, and/or waking too early. Stress, a health condition, pain, a medication, jet lag, and noise are some factors that can lead to disturbed sleep. Disturbed sleep can be acute (i.e., short-termed) or chronic in duration.

An individual with insomnia experiences frequent and long-term disturbed sleep with daytime impairment or distress despite having adequate opportunity and circumstance for sleep.

Disturbed sleep can have various negative consequences such as fatigue, lack of energy, initiative reduction, daytime sleepiness, tension headache, gastrointestinal symptoms, irritability, anxiety, mood disturbance, reduced motivation, and impairment in cognitive functions (attention, concentration, and memory).

Whether a subject has disturbed sleep or insomnia can be determined by a skilled practitioner in the art.

Controlled-Release Formulation

Described herein is a controlled-release formulation containing one or more compounds or compositions for aiding sleep (e.g., sedative or hypnotic agents).

Such compounds or compositions for aiding sleep include, but are not limited to, barbiturates (e.g., amobarbital (Amytal), pentobarbital (Nembutal), secobarbital (Seconal), and phenobarbital (Luminal); benzodiazepines (e.g., clonazepam (Klonopin N. America; Rivotril Europe, Asia), diazepam (Valium), estazolam (Prosom), flunitrazepam (Rohypnol), lorazepam (Ativan), midazolam (Versed), nitrazepam (Mogadon), oxazepam (Serax), triazolam (Halcion), temazepam (Restoril, Normison, Planum, Tenox, and Temaze), chlordiazepoxide (Librium), and alprazolam (Xanax)); non-benzodiazepine "Z-drugs" sedatives (e.g., eszopiclone (Lunesta), zaleplon (Sonata), zolpidem (Ambien), and zopiclone (Imovane, Zimovane)); antihistamines (e.g., diphenhydramine, dimenhydrinate, doxylamine, mirtazapine, and promethazine); plant components or extracts (e.g., components or extracts from *Duboisia hopwoodii*, chamomile, *Prostanthera striatiflora*, catnip, kava (*Piper methysticum*), valerian, *cannabis*, and *passiflora* (e.g., *Passiflora incarnata*)); Validol; chloral hydrate; trazodone; opiates and opioids; Suvorexant (MK-4305, Merck & Co.); glutethimide; and γ-hydroxybutyric acid. Other sedatives or hypnotic agents that target neurotransmitter receptors (e.g., histamine, GABA, and orexin receptors) can also be used in the formulation.

In one embodiment, the controlled-release formulation is formulated to release one compound/composition or one combination of compounds/compositions for aiding sleep. The formulation releases the compound/composition or combination of compounds/compositions at multiple stages (e.g., 2 to 12 stages). Each stage initiates release of the compound/composition or combination of compounds/compositions at a specific time after administration of the formulation.

For example, the formulation can release a first dose of a compound immediately, release a second dose of the same compound 1 hour after release of the first dose, and then release a third dose of the compound 2 hours after release of the second dose.

In one embodiment, the controlled-release formulation releases two or more compounds/compositions or combinations of compounds/compositions for aiding sleep. The formulation releases the compounds or compositions at multiple stages (e.g., 2 to 12 stages). Each stage initiates release of a specific compound/composition or combination of compounds/compositions at a specific time after administration of the formulation to a subject.

For example, the formulation can release immediately a first compound, release a second compound 30 minutes after the release of the first compound, and then release a third compound and a fourth compound together 3.5 hours after the release of the second compound. In another example, the formulation can release a first compound at time 0, 2 hours, 4 hours, and 6 hours, and a second compound at time 1 hour, 3 hours, 5 hours, and 7 hours.

The time interval between the initiation of each stage of release can be 30 minutes to 23 hours (e.g., 30 minutes, 1 hour, 1.5 hours, 2 hours, 3 hours, 3.5 hours, 4 hours, 4.5 hours, 5 hours, 5.5 hours, 6 hours, 6.5 hours, 7 hours, 8 hours, 9 hours, 10 hours, 12.5 hours, 13 hours, 15 hours, 20 hours, 22 hours, and 23 hours). Each stage can release a dose of a compound in the range of 0.01 mg to 100 mg (e.g., 0.01 mg, 0.05 mg, 0.1 mg, 0.25 mg, 0.5 mg, 1 mg, 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, and 100 mg).

The first stage of release can be an immediate release, in which release of one or more active agents is initiated shortly (e.g., within 30 minutes) after administration of the formulation. The first stage of release can also be a delayed released.

The above-described controlled-release formulation can be a tablet (e.g., a pill) or a capsule (e.g., a hard-shelled capsule or a softgel) for oral administration. Other formulations such as implants and patches can also be used.

Methods for formulating and making controlled-release formulations are known in the art. See, e.g., Hong Wen and Kinam Park, 2010, *Oral Controlled Release Formulation Design and Drug Delivery: Theory to Practice*, John Wiley & Sons, Inc. For example, controlled-release formulations can be designed based on particular physical mechanisms, e.g., dissolution, diffusion, osmosis, and ion exchange.

In a dissolution system, a drug is surrounded by or distributed in a polymeric composition (e.g., a polymeric membrane or a polymeric matrix). The drug is released when the polymeric composition dissolves. Properties of the polymeric composition, e.g., thickness and dissolution rate, determine drug release. In a diffusion system, the active ingredient has to diffuse through a polymeric composition (e.g., a polymeric membrane or a polymeric matrix) in order to be released. In an osmosis-based formulation, the drug is encapsulated by a polymeric coating that swells and erupts from osmotic pressure, thereby releasing the drug. Ion exchange formulation relies on attaching drug molecules to ionic groups. The drug molecules are then displaced by other ions and released. The controlled-release formulation described herein can utilize one release mechanism or a combination of release mechanisms.

In one embodiment, the above-described controlled-release formulation can be a tablet with multiple cores or layers. For example, the drug or combination of drugs for each stage of release can be surrounded by polymeric layer. The drug or combination of drugs is released as the layer dissolves.

In one embodiment, a multiparticulate system is employed. In this system, the active compounds are each delivered in multiple particles (e.g., small beads or microspheres ranging from 0.05 to 3.00 mm in size), each particle exhibiting the desired characteristics (e.g., release time and rate). For example, the above-described controlled-release formulation can include a plurality of particles. Each particle contains a core including a compound or combination of compounds for aiding sleep and a controlled-release polymeric composition (containing one or more polymers) encapsulating the core. Properties of the controlled-release polymeric composition in each particle determine the drug release profile of each particle. The formulation can include uncoated particles for immediate release of a drug. Any of the above-described or other release mechanisms (e.g., dissolution, diffusion, and osmosis) can be employed in a multiparticulate system. The plurality of particles can be encapsulated in a capsule or compressed into a tablet for oral administration. For example, a three-stage release formulation can contain three types of particles, each type for each stage of release. Each dose of a drug for each stage of release is delivered by multiple particles.

Natural and synthetic polymers for controlled-release formulations are known in the art. Such polymers include, but are not limited to, proteins, polysaccharides, nucleotides, alginate, chitosan, heparin, xanthan gum, starch, pectin, gelatin, kit-carrageenan, hydroxypropylmethylcellulose, hydroxypropylcellulose, hydroxyethylcellulose, ethycellulose, methylcellulose, polyvinyl alcohol, polyacrylic acid, polyethylene oxide, poloxamers, pluronics, polymethacrylate, cellulose, collagen, nylon, polyalkylcyanoacrylate, polyethylene, polyethylene-co-vinylacetate, polyhydroxythyl methacrylate, polyhydroxypropylethyl methacrylate, polymethyl methacrylate, polyurethane, and silicon. Commercially available polymers for pharmaceutical applications include EUDRAGIT® polymethacrylates.

In one embodiment, the controlled-release formulation employs an enteric coating or other coatings for delaying drug release until the drug reaches the small intestine or the colon. Delaying drug release in this manner would also control drug release time. Such coatings are known in the art.

When a compound or composition is released, it becomes available to the body. Each stage of release can have a specific release rate. For example, a stage can have a pulsatile-release profile, in which a drug is released rapidly and completely following a period of no release. A stage can also have a first-order release rate, in which a drug is released at a decreasing release rate. A zero-order release rate, i.e., a constant release rate, can also be employed. An entire dose (or a significant portion thereof) of a compound can be released within a short period or over an extended period. For example, the formulation can be designed to release at least 50% (e.g., more than 60%, 70%, 75%, 80%, 85%, 90%, or 95%) of a dose of a compound within 30 minutes of the initiation of release.

The controlled-release formulation can also include one or more pharmaceutical excipients, e.g., binders, plasticizers, lubricants, diluents, fillers, coloring agents, flavoring agents, glidants, and preservatives.

The controlled-release formulation can be administered to a patient daily or as needed to induce and maintains sleep.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

EXAMPLE 1

A Three-Stage Release Formulation

A formulation, in tablet or capsule form, releases drugs at three stages. At the first stage, release of 50 mg of Benadryl starts immediately after uptake. At the second stage, release of 5 mg of Ambien starts 2-3 hours after the initiation of the release of Benadryl. 2-3 hours after the start of the second stage, release of 0.5 mg of Activan is initiated.

EXAMPLE 2

A Three-Stage Release Formulation

A formulation, in tablet or capsule form, is formulated to initiate immediate release of 50 mg of Benadryl, 10 mg of melatonin, and 25 mg of Theanine upon uptake. 2 hours thereafter, release of 5 mg of Ambien is initiated. 3 hours after the start of the release of Ambien, release of 0.5 mg of Activan and 1 mg of Xanax are initiated.

EXAMPLE 3

In Vitro Release Profile of a Three-Stage Release Formulation

Hard gelatin capsules for releasing diphenhydramine HCl (i.e., 2-(diphenylmethoxy)-N,N-dimethylethanamine), zolpidem tartrate (i.e., N,N-dimethyl-2-(6-methyl-2-p-tolylimidazo[1,2-a]pyridin-3-yl)acetamide), and lorazepam (i.e., (RS)-7-Chloro-5-(2-chlorophenyl)-3-hydroxy-1,3-dihydro-2H-1,4-benzodiazepin-2-one) were manufactured.

The capsules were designed to release the three drugs in a staged sequence controlled via pH-dependent coatings: uncoated diphenhydramine HCl for immediate release, coated zolpidem for release about 2 hours after administration, and coated lorazepam for release about 4 hours after administration.

Each capsule contained the following agents: (1) 50 mg of uncoated diphenhydramine HCl; (2) 5 mg of zolpidem tartrate in multiparticulate form coated with EUDRAGIT® L30 D-55, which dissolves at above pH 5.5 (with half-maximal drug release at pH 5.8 and maximal release at pH 6.3); and (3) 0.5 mg of lorazepam in multiparticulate form coated with EUDRAGIT® L/S 12.5 (1:1), which dissolves at above pH 6.5 (with half-maximal drug release at pH 7.2). The coatings were selected to achieve release of zolpidem tartrate with gastric emptying and release of lorazepam when the drug reaches the intestines.

Six capsules were individually tested in beakers for pH-dependent release of each active agent. As shown in Table 1, at pH 2, more than 89% of diphenhydramine HCl was released within 30 minutes, whereas neither zolpidem tartrate nor lorazepam was released. At pH 6.4, more than 71% of zolpidem tartrate, but not lorazepam, was released within 30 minutes. At pH 7.2, more than 70% of lorazepam was released within 30 minutes.

TABLE 1 pH-dependent release of diphenhydramine, zolpidem, and lorazepam from capsules.

| | At 30 min in pH 2 (At time zero pH 2) % Release | | | At 150 min in pH 6.4 (At 120 min changed to pH 6.4) % Release | | | At 270 min in pH 7.2 (At 240 min changed to pH 7.2) % Release | | |
|---|---|---|---|---|---|---|---|---|---|
| Cap# | Diph | Zolp | Lora | Diph | Zolp | Lora | Diph | Zolp | Lora |
| 1 | 93.4 | 0 | 0 | 98.0 | 76.4 | 0 | 99.9 | 91.0 | 81.3 |
| 2 | 89.8 | 0 | 0 | 100 | 68.2 | 0 | 100 | 98.7 | 77.2 |
| 3 | 98.2 | 0 | 0 | 99.9 | 79.4 | 0 | 99.8 | 99.1 | 80.1 |
| 4 | 98.7 | 0 | 0 | 100 | 76.2 | 0 | 99.1 | 100 | 83.2 |
| 5 | 96.8 | 0 | 0 | 100 | 71.3 | 0 | 100 | 97.6 | 70.2 |
| 6 | 97.3 | 0 | 0 | 99.9 | 80.1 | 0 | 99.2 | 99.1 | 72.1 |

Diph: diphenhydramine
Zolp: zolpidem
Lora: lorazepam

EXAMPLE 4

Sleep Study in Dogs

The capsules described in Example 3 above were tested in dogs at CARE Research in Fort Collins, Colo. Sleep pattern of dogs is polyphasic. Each bout of sleep ranges from a few minutes to about 45 minutes. Dogs follow circadian rhythm. They fall asleep from time to time during day-time but gain most of their needed sleep during night-time.

On Day 1, four normal, untreated Beagle dogs were housed individually and monitored by video-cameras mounted above continuously for 24 hours.

On Day 3, each dog was orally fed with one capsule in the morning, housed individually in the same room as in Day 1, and monitored by video-cameras mounted above continuously for 24 hours.

Recorded videos from 12 noon to 8 pm on Day 1 and Day 3 were analyzed. Time of each sleep bout by each dog was measured and total sleep time of each dog in the course of 8 hours was tallied. Table 2 below summarizes the test results.

As shown in Table 2, the capsules led to a significant increase in total sleep time in all four treated Beagle dogs.

TABLE 2

Effects of capsules on total sleep time in Beagle dogs.

| | Total Sleep Time | | Difference between Day 1 and Day 3 | |
|---|---|---|---|---|
| Dog # | Day 1 Placebo | Day 3 Treated | Increase (min) | % Increase |
| 1501 | 152 min | 288 min | 136 min | 89.5% |
| 1502 | 128 min | 280 min | 152 min | 118.8% |
| 1503 | 145 min | 256 min | 111 min | 76.6% |
| 1504 | 160 min | 297 min | 137 min | 85.6% |

EXAMPLE 5

Sleep Study in Human Subjects

For human studies, hard gelatin capsules identical to those described in Example 3 were manufactured, except that lorazepam was coated with EUDRAGIT® L 12.5 instead of EUDRAGIT® L/S 12.5 (1.1) to account for the slight differences between the gastrointestinal pHs of dogs and humans. EUDRAGIT® L 12.5 dissolves at above pH 6.0.

It is anticipated that, after administration of the capsules to human subjects, diphenhydramine would be released immediately and be effective for up to 4 hours. Zolpidem would be released about 2 hours after administration and reach its $t_{max}$ (i.e., time to maximum concentration in plasma) about 2 hours later. Lorazepam would be released about 4 hours after administration of the capsules and reach its $t_{max}$ about 6 hours post administration.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

The invention claimed is:

1. A controlled-release formulation, comprising 50 mg of diphenhydramine HCl, 5 mg of zolpidem tartrate, and 0.5 mg of lorazepam, wherein the formulation is formulated for a first stage immediate release of the diphenhydramine HCl in a subject after the formulation is administered to the subject, a second stage release of the zolpidem tartrate that starts 2-3 hours after initiation of the first stage, and a third stage release of the lorazepam that starts 2-3 hours after initiation of the second stage.

2. The formulation of claim 1, wherein the formulation is a tablet or capsule for oral administration.

3. The formulation of claim 2, wherein the tablet or capsule contains a plurality of particles, each particle including a drug core and a polymeric composition encapsulating the core, wherein each drug core contains zolpidem tartrate or lorazepam.

4. The formulation of claim 3, wherein the polymeric composition includes a polymethacrylate.

5. The formulation of claim 3, wherein the formulation contains diphenhydramine HCl, zolpidem tartrate, and lorazepam as the only three active compounds.

6. The formulation of claim 5, wherein the polymeric composition encapsulating the drug core containing zolpidem tartrate dissolves at above pH 5.5 and the polymeric composition encapsulating the drug core containing lorazepam dissolves at above pH 6.5, the diphenhydramine HCl being uncoated.

7. A method of treating disturbed sleep or insomnia in a subject, comprising administering the formulation of claim 1 to a subject in need thereof.

* * * * *